United States Patent [19]

Fehr

[11] Patent Number: 5,011,844
[45] Date of Patent: Apr. 30, 1991

[54] SUBSTITUTED 4-AZATRICYCLO(22.3.1.0$^{4,9}$)OCTACOS-18-ENE DERIVATIVES, THEIR PREPARATION AND PHARMACEUTICAL COMPOSITIONS CONTAINING THEM

[75] Inventor: Theodor Fehr, Dornach, Switzerland

[73] Assignee: Sandoz Ltd., Basel, Switzerland

[21] Appl. No.: 399,673

[22] Filed: Aug. 25, 1989

[30] Foreign Application Priority Data

Aug. 26, 1988 [GB] United Kingdom ............... 8820348
May 31, 1989 [GB] United Kingdom ............... 8912432

[51] Int. Cl.$^5$ ................ A61K 31/395; C07D 498/16; C12P 17/18
[52] U.S. Cl. ................. 514/291; 514/411; 540/456; 435/898; 435/886; 435/118
[58] Field of Search ............ 540/456; 514/63, 183, 514/291, 411; 435/598, 886, 118

[56] References Cited

U.S. PATENT DOCUMENTS 4,894,366 1/1990 Okuhara et al. .................. 540/456

OTHER PUBLICATIONS

Jones et al., "J. Am. Chem. Soc." (1989), vol. III, pp. 1157–1159.

*Primary Examiner*—Robert T. Bond
*Attorney, Agent, or Firm*—Gerald D. Sharkin; Robert S. Honor; Thomas O. McGovern

[57] ABSTRACT

The compounds of formula I

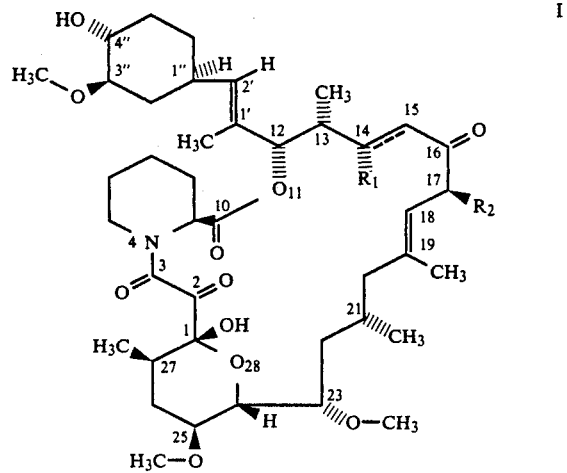

wherein
either
$R_1$ is hydroxy,
$R_2$ is allyl or n-propyl and
there is a single bond between the carbon atoms numbered 14 and 15
or
$R_1$ is missing,
$R_2$ is allyl and
there is a double bond between the carbon atoms numbered 14 and 15,
have interesting immunosuppressant and anti-inflammatory properties.

They are obtained by fermentation or synthesis, e.g. by hydrogenation or dehydration.

9 Claims, 4 Drawing Sheets

SUBSTITUTED 4-AZATRICYCLO(22.3.1.0⁴,⁹)OCTACOS-18-ENE DERIVATIVES, THEIR PREPARATION AND PHARMACEUTICAL COMPOSITIONS CONTAINING THEM

FIELD

The invention relates to the field of natural product chemistry, in particular the chemistry of macrolides. The invention concerns a compound of formula I

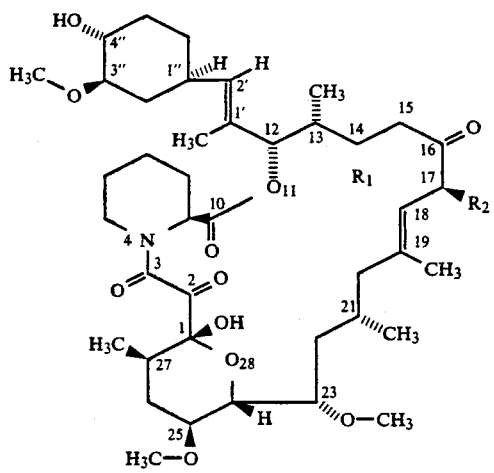

wherein
either
$R_1$ is hydroxy,
$R_2$ is allyl or n-propyl and there is a single bond between the carbon atoms numbered 14 and 15
or
$R_1$ is missing,
$R_2$ is allyl and
there is a double bond between the carbon atoms numbered 14 and 15.

Formula I is meant to cover the compounds in free form and, where such forms may exist, in salt form.

BACKGROUND ART

Fujisawa EP 184162 discloses a group of compounds represented by formula A

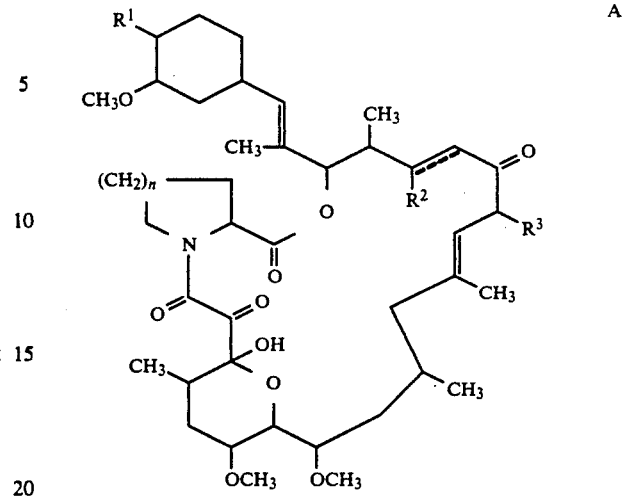

wherein
$R^1$ is hydroxy or protected hydroxy,
$R^2$ is hydrogen, hydroxy or protected hydroxy,
$R^3$ is methyl, ethyl, propyl or allyl,
n is an integer of 1 or 2 and the symbol of a line and dotted line is a single bond or a double bond,
and salts thereof.

As is evident from the above formula, there are many asymmetry centers and therefore, a large number of possible stereoisomers exist for any given meaning of the substituents.

On the other hand, although on page 4 in EP 184 162 it is mentioned that there may be one or more coniormer(s) or stereoisomeric pairs such as optical and geometrical isomers due to asymmetric carbon atom(s) and double bond(s), for none of the compounds specifically disclosed in EP 184 162 is there any indication of the exact stereochemical configuration.

This is so in particular for the compound named FK 900506 (FK 506), which is the object of Examples 1 to 3 therein, its derivative hydrogenated at the allyl group to an n-propyl group, which is the object of Example 21 therein, and its derivative dehydrated between positions 14 and 15, which is disclosed in Example 17 therein. From the formula and the names indicated on page 32, 95 and 98 of EP 184 162 it is not apparent what confiuration FK 506 and these two derivatives have.

The configuration of FK 506 has however been published in the scientific literature, e.g. in H. Tanaka et al., J. Am. Chem. Soc. 109 (1987) 5031-5033, T. Kino et al., J. Antibiotics 40 (1987) 1249-1255 and T. Taga et al., Acta Cryst. C43 (1987) 751-753.

It appears therefrom that FK 506 and, by implication, the two derivatives thereof mentioned above, have the configuration indicated above for formula I of the present invention, except that at the carbon atom numbered 17 the configuration is reversed, i.e. it is the R configuration, whereas in formula I above the S configuration is shown.

SUMMARY

It has now been found that, surprisingly, the compounds of formula I, which are novel and are the stereoisomers of FK 506, its dihydrogenated derivative and its dehydrated derivative, but with the opposite configuration at the carbon atom in position 17, have an excellent immunosuppressant and antiinflammatory, e.g. antipsoriatic activity.

DETAILED DESCRIPTION

The compounds of formula I are novel. They may be prepared in accordance with standard procedures.

The compounds of formula I wherein $R_1$ is hydroxy and $R_2$ is allyl (Compound No. 1; "17-epi-FK506") or wherein $R_2$ is missing and $R_2$ is allyl (Compound No. 3; "dehydro-17-epi-FK506") may be isolated in known manner from e.g. Streptomyces tsukubaensis No. 9993 using the general procedures described in EP 184 162 and in the Examples hereafter. Thus, an appropriate Streptomyces strain such as Streptomyces tsukubaensis No. 9993 may be cultivated in an appropriate culture medium and the above two compounds isolated from the resultant culture. Cultivation is effected by incubation, e.g. as described in EP 184 162 or in Example 1 hereunder. The pH is kept between about 6 and about 8, preferably at about 6.8. The temperature may vary between about 18° C. and about 35° C., it preierably is kept at around 27° C.

The compound of formula I wherein $R_1$ is hydroxy and $R_2$ is n-propyl (Compound No. 2; "dihydro-17-epi-FK506") may e.g. be prepared in known manner by hydrogenation of Compound No. 1, e.g. by catalytic reduction using palladium on charcoal as a catalyst. The temperature may e.g. vary from about 5° C. to about 30° C., preferably about room temperature is used. The reaction is preferably effected in the presence of an inert organic solvent such as an alcohol, e.g. ethanol.

Compound No. 3 may e.g. also be prepared in known manner by dehydration of Compound No. 1, e.g. by catalytic dehydration in an acidic solution. Preferably an inert organic solvent such as an ester, e.g. acetic acid ethyl ester, is used. The temperature may vary between about 5° C. and about 30° C., the reaction preferably is effected at about room temperature.

The compounds of the invention may be isolated and purified from the reaction or isolation mixture in known manner.

The producing strain, Streptomyces tsukubaensis No. 9993, is disclosed in Fujisawa EP 184162. Samples are available from the Fermentation Research Institute, Tsukuba, Ibaraki 305, Japan under the provisions of the Budapest Treaty, under deposit No. FERM BP-927. This strain has been redeposited on April 27, 1989 with the Agricultural Research Culture Collection International Depository, Peoria, Ill. 61604, USA under the provisions of the Budapest Treaty, under deposit No. NRRL 18488.

Compound No. 1 may e.g. also be produced by total synthesis according to the procedure published for the total synthesis of FK 506 (T. K. Jones et al., *J. Am. Chem. Soc.* 111 [1989]1157–1159) using corresponding epimeric starting materials.

The invention thus concerns the compounds of formula I as defined above.

It also concerns a process for the preparation of a compound of formula I as defined above which comprises
(a) for the preparation of the compounds of formula I wherein
  $R_1$ is hydroxy or missing and $R_2$ is allyl,
cultivating an appropriate Streptomyces strain such as Streptomyces tsukubaensis No. 9993 and isolating the compounds from the resultant mixture, (b) for the preparation of the compound of formula I wherein
  $R_1$ is missing and $R_2$ is allyl,
dehydrating the corresponding compound of formula I wherein
  $R_1$ is hydroxy or
(c) for the preparation of the compound of formula I wherein
  $R_1$ is hydroxy and $R_2$ is n-propyl,
hydrogenating the corresponding compound of formula I wherein
  $R_2$ is allyl.

The invention also concerns a pharmaceutical composition containing a compound of formula I as defined above together with a pharmaceutically acceptable carrier or diluent.

It also concerns a compound of formula I as defined above for use as a pharmaceutical.

It also concerns the use of a compound of formula I as defined above in the preparation of a pharmaceutical composition, comprising mixing a compound of formula I with a pharmaceutically acceptable carrier or diluent.

It further concerns a process for the preparation of a pharmaceutical composition comprising mixing a compound of formula I as defined above with a pharmaceutically acceptable carrier or diluent.

It further concerns a method for the prevention or treatment of conditions requiring immunosuppression or of inflammatory conditions, comprising administering a therapeutically effective amount of a compound of formula I as defined above together with a pharmaceutically acceptable carrier or diluent to a subject in need of such treatment, e.g. a method of treatment of immune-mediated conditions of the eye comprising topically administering to the eye surface a therapeutically effective amount of a compound of formula I as defined above in a pharmaceutically acceptable ophthalmic vehicle. DR

Figure 1:
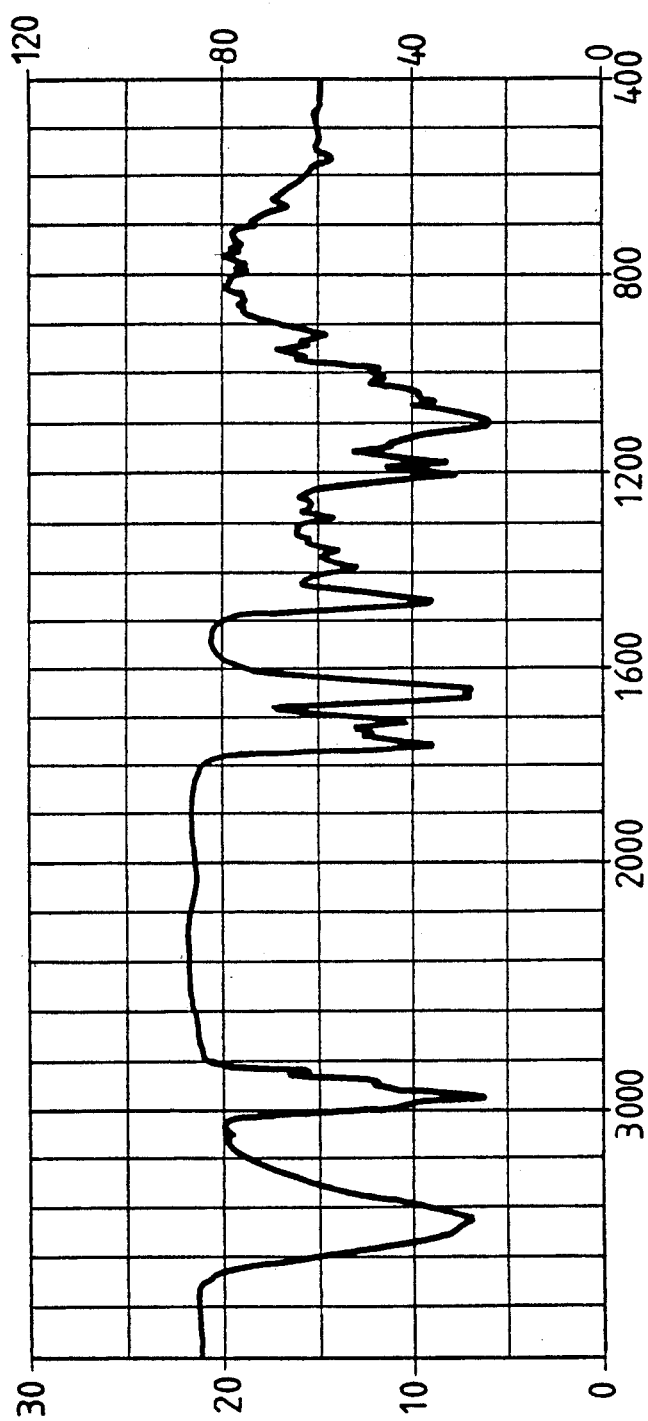
FIG. 1: IR-spectrum of Compound No. 1.

The following Examples illustrate the invention and are not limitative.

EXAMPLE 1

Fermentation process variant (a), cultivation (A) Starting culture on agar

An agar culture of strain Streptomyces tsukubaensis No. 9993 is grown for 14 days at 27° C. on the following medium:

| Yeast extract (Bacto) | 4.0 g |
| Malt extract (Bacto) | 10.0 g |
| Dextrose (Bacto) | 4.0 g |
| Agar (Bacto) | 20.0 g |
| demineralised water ad | 1000 ml |

The pH value is set to 6.6 with $NaOH/H_2SO_4$ prior to sterilization. Sterilization is effected for 20 minutes at 120° C.

(B) Preculture

The spores and mycelium from 6 starting cultures are suspended in 90 ml of a 0.9 % solution of sodium chloride. erlenmeyer flasks containing each 1 liter of preculture medium are inoculated with 7 ml of this suspension. The preculture medium has the following composition:

| | |
|---|---|
| Glycerine | 10.0 g |
| Starch | 10.0 g |
| Glucose | 5.0 g |
| Cotton seed extract (Pharmamedia) | 10.0 g |
| Yeast extract (Gistex) | 5.0 g |
| $CaCO_3$ | 2.0 g |
| demineralised water ad | 1000 ml |

The pH value is set to 6.8 prior to sterilization, which takes place for 20 minutes at 120° C.

The propagation of this preculture is effected for 96 hours at 27° C. at 200 rpm on an agitator with an excentricity of 50 mm.

(C) Intermediate culture

Two 500 1 aliquots of preculture medium are inoculated in a 750 l steel fermentor with 5 liters each of preculture and incubated for 48 hours at 27° C. Rotation speed is 100 rpm and aeration is 0.5 l per minute per liter of medium.

(D) Main culture 6000 l of main culture medium are inoculated in two 4500 l steel fermentors with 600 l of intermediate culture. The main culture medium has the following composition:

| | |
|---|---|
| Soluble starch | 45.0 g |
| Corn steep (Roquette) | 10.0 g |
| Yeast extract (Gistex) | 10.0 g |
| $CaCO_3$ | 1.0 g |
| demineralised water ad | 1000 ml |

The pH is set to 6.8 with NaOH prior to sterilization. The corn steep is presterilized for 20 minutes at 120° C. Sterilization of the whole medium is effected at 120° C. for 20 minutes.

Incubation is effected for 96 hours at 27° C, 50 rpm, 0.5 bar and an aeration rate of 0.5 l per minute per liter of medium. Foam formation is reduced using a silicone antifoam agent.

EXAMPLE 2

17β-Allyl-1β,14α-dihydroxy-12-[2'-(4''(R)-hydroxy-3''(R)-methoxycyclohex-1''(R)-yl)-1'-methyl-trans-vinyl]-23α25β-dimethoxy-13α,19,21α,27β-tetramethyl11,28-dioxa-4-azatricyclo [22.3.1.0$^{4,9}$]octacos-18-trans-ene-2,3,10,16-tetraone

[32 Compound No. 1; "17-epi-FK506"

[Formula I: $R_1$=OH; $R_2$=allyl; single bond in 14,15-position

[process variant (a), isolation ]

Figure 2:
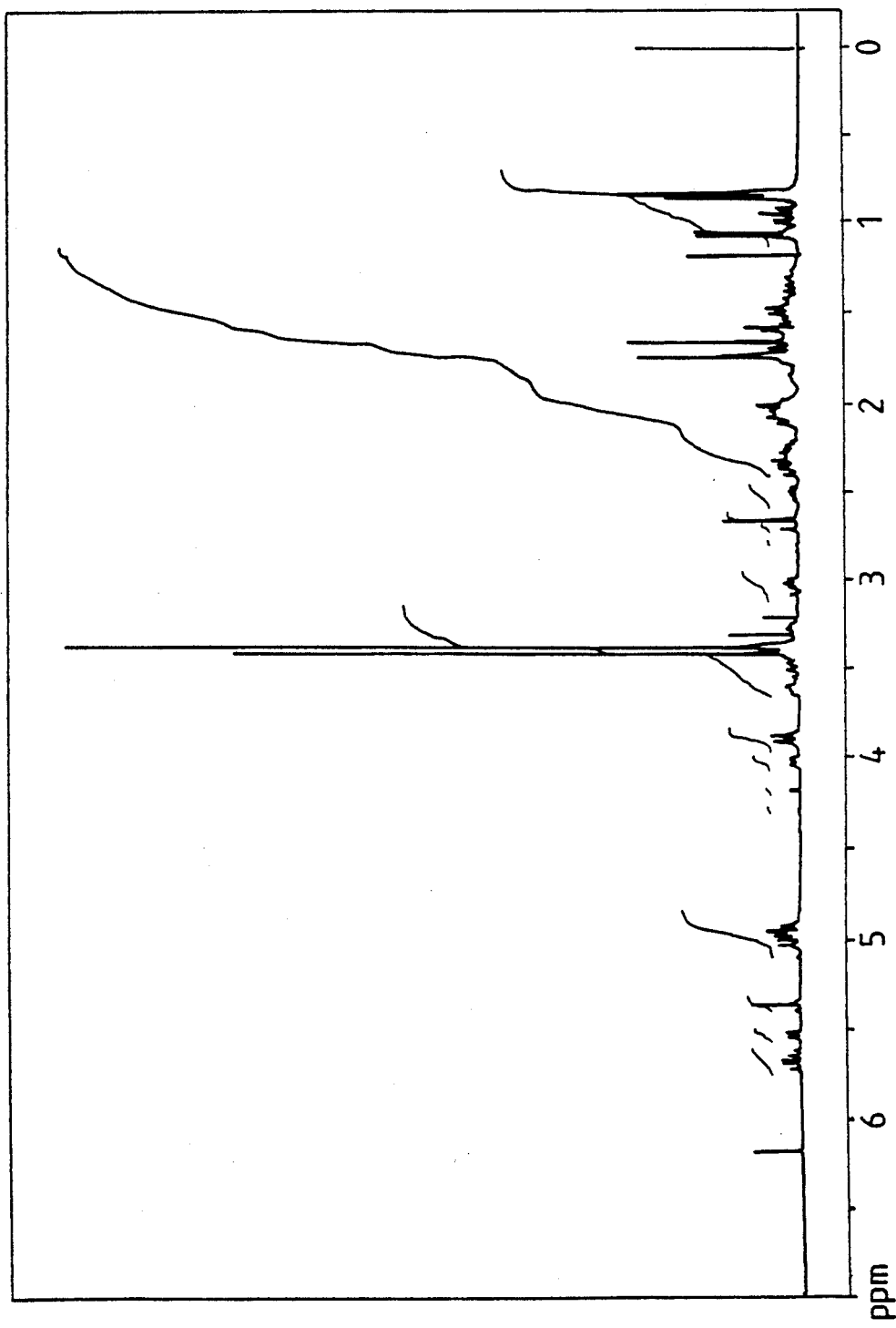
FIG. 2: NMR-spectrum of Compound No. 1.

6200 l of fermentation medium are stirred for 6 hours at room temperature with 6000 l of ethyl acetate and thereafter the two phases are separated in a separator. The ethyl acetate phase is evaporated to dryness under reduced pressure. The extract is then defatted by separation with thrice 70 l of methanol/water 9:1 and thrice 70 l of hexane. The methanol/water phase is then evaporated to dryness under reduced pressure and the residue is chromatographed on a column containing 25 kg Sephadex LH20 in methanol and then on a column containing 20 kg silicagel Merck (0.04 to 0.063 mm) using tert-butylmethylether as an eluent. After 50 l of elution, fractions of 6.2 l are collected. Fractions 11 to 13 contain mainly FK506. Fractions 14 to 16 are collected and brought to crystallization by dissolution in 150 ml of ether and addition of 100 ml of hexane. The product is recrystallized from acetonitrile. The title compound (Compound No. 1) is obtained. It has the following characteristics:

M.P. 180°–184° C. (dec.) (from methanol, ether or acetonitrile),
colorless crystals,
$[\alpha]_D^{22}$ = −4.0° (c=0.72 in methanol),
elementary analysis:
found C 65.6, H 8.7, N 1.8, O 24.0%;
calc. C 65.7, H 8.7, N 1.7, O 23.9%.
elementary formula: $C_{44}H_{69}NO_{12}$ (804.0),
mass spectrum FAB 804.5=(MH+),
786.5 (MH$^{30}$−8),
768.5 (MH$^{30}$−36),
576.3 (MH$^{30}$ −228,
100%
UV-spectrum in methanol: $\lambda_{max}$=end absorption (MeOH),
IR-spectrum in KBr: see FIG. 1,
$^1$H-NMR-spectrum in CDCL$_3$, 360 MHz with tetramethylsilane as internal standard: see FIG. 2.

The structure of this compound has also been analyzed by X-ray diffraction analysis and compared with that for FK 506. The structure was refined to an R factor of 0.046 using 3200 observed reflections. The main insight gained thereby is that the conformation of the 21-membered ring is stabilised by an intramolecular hydrogen bond (010 ... 022) and is significantly different from the ring conformation found in the published crystal structure of FK 506.

EXAMPLE 3

1β,14 α-Dihydroxy-12-[2'-(4''(R)-hydroxy-341 (R)-methoxycyclohex-1''(R)-yl)-1,-methyl-trans-vinyl]-23α,25β-dimethoxy-13α,19,21α27β-tetramethyl-17β17β-propyl-11,28-dioxa-4-azatricyclo[22.3.1.0$^{4,-9}$]octacos-18-trans-ene-2,3,10,16-tetraone

[=Compound No. 2; "dihydro-17-epi-FK506"]

[Formula I: $R_1$=OH; $R_2$=n-propyl; single bond in 14,15-position]

[process variant c), hydrogenation]

1.6 g of the Compound No. 1 is dissolved in 80 ml of ethanol, mixed with 80 mg of 10 % palladium on charcoal and hydrogenated for 10 minutes at normal pressure and room temperature. The catalyst is then filtered off, the filtrate evaporated to dryness, and the residue chromatographed with tert-butylmethylether on 180 g silicagel. The fractions are checked by high pressure liquid chromatography and the fractions containing the hydrogenation product are collected and crystallized from diethylether/hexane. The title compound (Compound No. 2) is obtained. It has the following characteristics:

M.P 154–156° C. (dec.):
$[\alpha]_D^{22}$: −19.1° (c=1.10 in methanol,

Elementary analysis: found: C 65., H 9.0, N 1.8, O 24.0 %; calc. C 65.6, H 8.9, N 1.7, O 23.8 %;

Elementary formula: $C_{44}H_{71}NO_{12}$ (806.0),

Mass spectrum: FAB 806.9=(MH+), 788.9 (MH+ −18), 770.9 (MH+ −36), 578.6 (MH+ −228), 100 %.

UV-spectrum in methanol: $\lambda_{max}$=end absorption (MeOH).

Figure 3:
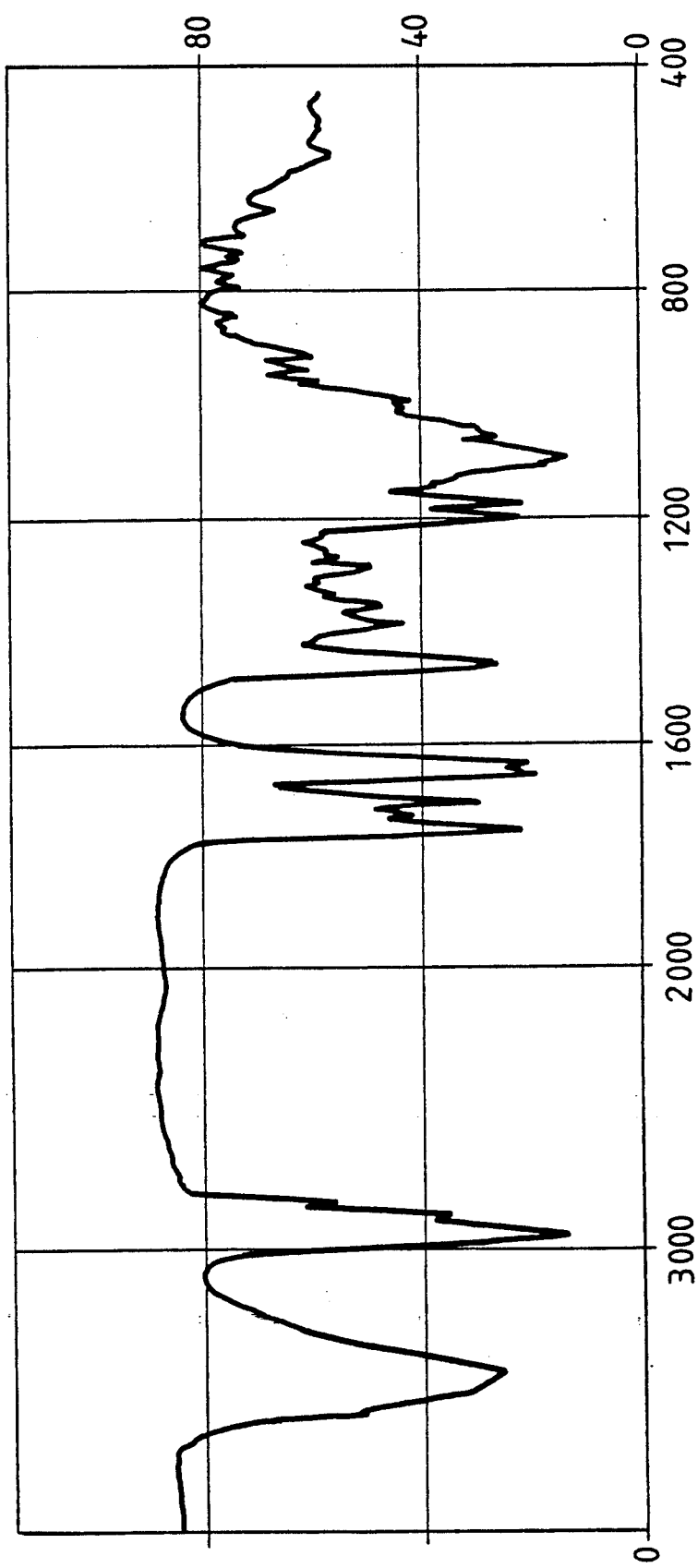
FIG. 3: IR-spectrum of Compound No. 2.

IR-spectrum in KBr: see FIG. 3.

Figure 4:
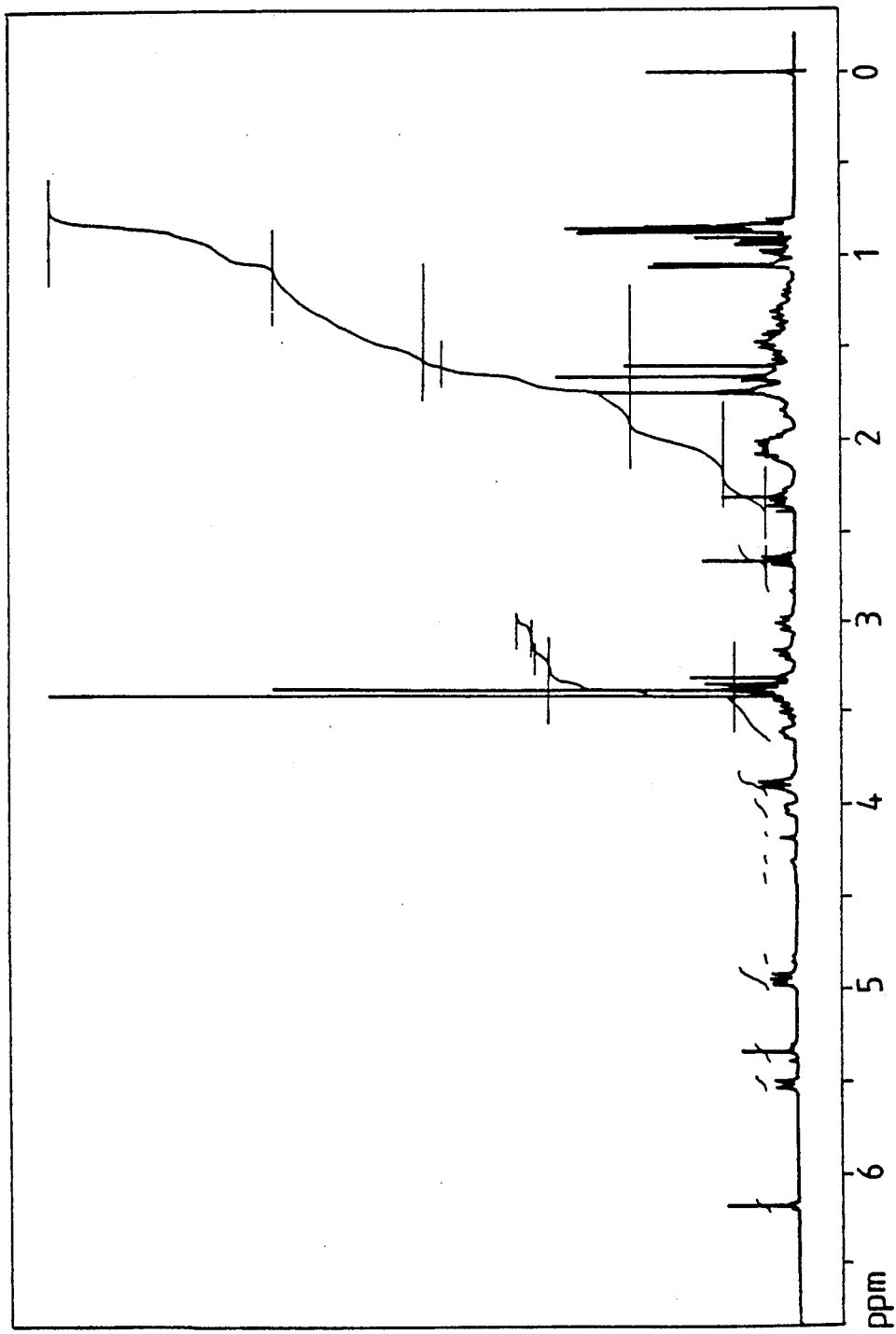
FIG. 4: NMR-spectrum of Compound No. 2.

$^1$H-NMR-spectrum in $CDCl_3$, 360 MHz with tetramethylsilane as internal standard: see FIG. 4.

EXAMPLE 4

17β-Allyl-1β-hydroxy-12-[2'-(4"(R)-hydroxy-3"(R)-methoxycyclohex-1"(R)-yl)-1'-methyl-trans-vinyl]-23α,25β-dimethoxy-13α, 19,21α,27β-tetramethyl-11,28-dioxa-4-azatricyclo [22.3.1.0$^{4,9}$]soctacos-14-trans,18-trans-diene-2,3,10,16-tetraone Compound No. 3; "dehydro-17-epi-FK506"]

[Formula I: $R_1$ missing; $R_2$=allyl; double bond in 14,15-position]

(a) Synthetically [process variant (b), dehydration] :

1 g Compound No. 1 is dissolved in 1 l of ethyl acetate and 10 ml 1N HCl are added. Agitation is maintained for 5 days. Then the reaction mixture is neutralized with 10 ml of IN NaOH and washed with 500 ml of water. The organic phase is dried over sodium sulfate and evaporated to dryness. The residue is subjected to chromatographic separation over silicagel H using methyl tert-butylether as an eluent. The fractions are checked by HPLC. The product is recrystallized from ether. The title compound (Compound No. 3) is obtained. It has the following characteristics:

M.P. 189°-191° C. (from ether).
colourless crystals.
$[\alpha]_D^{22}$=131.9° (c=0.84 in $CHCl_3$).
elementary formula: $C_{44}H_{67}NO_{11}$ (786.0).
UV-spectrum in methanol: $\lambda_{max}$ 230 log $\epsilon'$=1.2115; 323 log $\epsilon'$=0.2138.
retention time upon high pressure liquid chromatography (HPLC)
in gradient 1 (in 20 min from 50:50 to 10:90): 16.64 min.
in gradient 2 (in 20 min from 90:10 to 10:90): 22.48 min.
HPLC system: column: Lichrosorb RP18 Merck (250×4 mm); flow rate: 2 ml/min; detection UV 220 nm/0.1;
solvents: buffer triethylamine-phosphate pH 3.5 0.05 M 10 % acetonitrile / acetonitrile (b) By fermentation (process variant a), isolation]

After crystallization of FK506 from fractions 11 to 13 (see Example 2) the supernatant is chromatographed over silicagel using hexane/methyl tert-butylether/methanol 5:4:1 as an eluent. The fractions are checked by HPLC and the fraction having a retention time of 17.25 min is rechromatographed over silicagel H with methyl tert-butylether. Upon recrystallization from ether the title compound is obtained (M.P. 189°-193° C.).

The compounds of the invention possess pharmacological activity. They are, therefore, useful as pharmaceuticals.

In particular, they possess immunosuppressant and anti-inflammatory activity.

As regards immunosuppressant activity, in the mixed lymphocyte reaction [T. Meo, *Immunological Methods*, L. Lefkovits and B. Permis, Eds., Academic Press, N.Y. (1979) p. 227-239], they elicit suppression of mixed lymphocytes at a dosage of from about 0.15 nM to about 10 nM. They are further active at a concentration of from about 0.5 nM to about 10 nM in the test of the primary humoral immune response on sheep red blood cells in vitro (R.I. Mishell and R. W. Dutton, *Science* 153 [1966]1004-1006; R. I. Mishell and R. W. Dutton, *J. Exp. Med.* 126 [1967]423-442).

As regards anti-inflammatory activity, in the oxazolone allergy test (mouse) (described in EP 315978) the compounds elicit an activity between 20% and 70% upon topical administration at a concentration of 0.01 %.

The compounds of formula I are therefore useful as immunosuppressant and antiinflammatory agents in the prevention and treatment of conditions requiring immunosuppression and of inflammatory conditions, such as (a) the prevention and treatment of
resistance in situations of organ or tissue transplantation, e.g. of heart, kidney, liver, bone marrow and skin,
graft-versus-host disease, such as followin bone marrow grafts,
autoimmune diseases such as rheumatoid arthritis, systemic Lupus erythematosus, Hashimoto's thyroidis, multiple sclerosis, Myasthenia gravis, diabetes type I and uveitis,
cutaneous manifestations of immunologically-mediated illnesses, such as Alopecia areata, and
(b) treatment of inflammatory and hyperproliferative skin diseases, such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and acne.

The compounds may be administered systemically or topically.

For these indications the appropriate dosage will, of course, vary depending upon, for example, the host, the mode of administration and the nature and severity of the condition being treated. However, in general, satisfactory results are indicated to be obtained systemically at daily dosages of from about 0.15 mg/kg to about 1.5 mg/kg animal body weight. For the larger mammal an indicated daily dosage is in the range from about 0.01 mg to about 100 mg of a compound of formula I, conveniently administered, for example, in divided doses up to four times a day.

For topical use satisfactory results are obtained with local administration of a 1-3 % concentration of active substance several times daily, e.g. 2 to 5 times daily. Examples of indicated galenical forms are lotions, gels and creams.

The compound of the invention may be administered by any conventional route, in particular enterally, e.g. orally, e.g. in the form of tablets or capsules, or topically, e.g. in the form of lotions, gels or creams.

Pharmaceutical compositions comprising a compound of formula I as defined above in association with at least one pharmaceutical acceptable carrier or diluent may be manufactured in conventional manner by mixing with a pharmaceutically acceptable carrier or diluent. Unit dosage forms contain, for example, from about 0.0025 mg to about 50 mg of a compound of formula I.

Topical administration is e.g. to the skin. A further form of topical administration is to the eye, for the treatment of immune-mediated conditions of the eye, such as: auto-immune diseases, e.g. uveitis, keratoplasty and chronic keratitis; allergic conditions, e.g. vernal conjunctivitis; inflammatory conditions and corneal transplants, by the topical administration to the eye surface of a compound of formula I as defined above in a pharmaceutically acceptable ophthalmic vehicle.

The ophthalmic vehicle is such that the compound of formula I is maintained in contact with the ocular surface for a sufficient time period to allow the compound to penetrate the corneal and internal regions of the eye, e.g. the anterior chamber, posterior chamber, vitreous body, aqueous humor, vitreous humor, cornea, iris/ciliary, lens, choroid/retina and sclera.

The pharmaceutically acceptable ophthalmic vehicle may be e.g. an ointment, vegetable oil, or an encapsulating material.

Compound No. 1 is preferred for the above systemic and topical indications.

I claim:

1. A compound of formula I

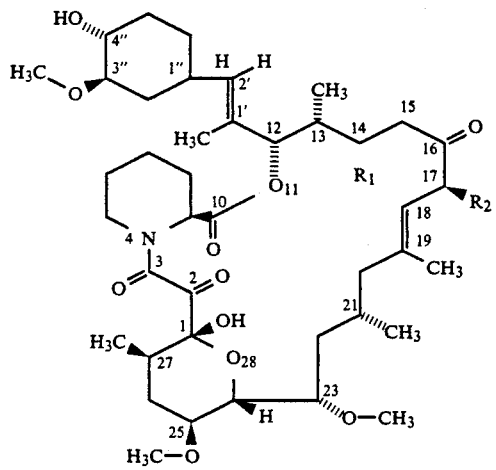

wherein
either
$R_1$ is hydroxy,
$R_2$ is allyl or n-propyl and
there is a single bond between the carbon atoms numbered 14 and 15

$R_1$ is missing,
$R_2$ is allyl and
there is a double bond between the carbon atoms numbered 14 and 15.

2. The compound according to claim 1 wherein $R_1$ is hydroxy, $R_2$ is allyl and there is a single bond between the carbon atoms numbered 14 and 15.

3. The compounds according to claim 1 wherein either
$R_1$ is hydroxy, $R_2$ is n-propyl and
there is a single bond between the carbon atoms numbered 14 and 15 or
$R_1$ is missing, $R_2$ is allyl and
there is a double bond between the carbon atoms numbered 14 and 15.

4. A process for the preparation of the compound of formula I wherein
$R_1$ is hydroxy, $R_2$ is n-propyl and
there is a single bond between the carbon atoms numbered 14 and 15
which comprises
hydrogenating the corresponding compound of formula I wherein $R_2$ is allyl.

5. A pharmaceutical composition containing a compound according to claim 1 together with a pharmaceutically acceptable carrier or diluent.

6. A method for the prevention or treatment of conditions requiring immunosuppression or of inflammatory conditions, such as
(a) the prevention and treatment of
resistance in situations oi organ or tissue transplantation e.g. of heart, kidney, liver, bone marrow and skin,
graft-versus-host disease, such as following bone marrow grafts,
autoimmune diseases such as rheumatoid arthritis, systemic Lupus erythematosus, Hashimoto's thyroidis, multiple sclerosis, Myasthenia gravis, diabetes type I and uveitis,
cutaneous manifestations of immunologically-mediated illnesses, such as Alopecia areata, and
(b) the treatment of inflammatory and hyperproliferative skin diseases, such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and acne, comprising administering a therapeutically effective amount of a compound according to claim 1 together with a pharmaceutically acceptable carrier or diluent to a subject in need of such treatment.

7. A method of treatment of immune-mediated conditions of the eye, such as: auto-immune diseases, e.g. uveitis, keratoplasty or chronic keratitis; allergic conditions, e.g. vernal conjunctivitis; inflammatory conditions or corneal transplants, which comprises topically administering to the eye surface a therapeutically effective amount of a compound according to claim 1 in a pharmaceutically acceptable ophthalmic vehicle.

8. A process for the preparation of a compound of claim 1 wherein $R_1$ is hydroxy or is missing and $R_2$ is allyl, which comprises cultivating an appropriate Streptomyces strain such as Streptomyces tsukubaensis No. 9993 until a sufficient amount of the compound is produced, and isolating the compound from the resulting culture.

9. A process for the preparation of a compound of claim 1 wherein $R_1$ is missing and $R_2$ is allyl, which comprises dehydrating the corresponding compound of claim 1 in which $R_1$ is hydroxy and isolating the compound.

* * * * *